United States Patent
Kamikawa et al.

(10) Patent No.: US 11,813,747 B2
(45) Date of Patent: Nov. 14, 2023

(54) LINK STRUCTURE

(71) Applicant: SONY CORPORATION, Tokyo (JP)

(72) Inventors: Yasuhisa Kamikawa, Tokyo (JP); Yasunori Kawanami, Tokyo (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 17/250,522

(22) PCT Filed: Jul. 29, 2019

(86) PCT No.: PCT/JP2019/029633
§ 371 (c)(1),
(2) Date: Jan. 31, 2021

(87) PCT Pub. No.: WO2020/031772
PCT Pub. Date: Feb. 13, 2020

(65) Prior Publication Data
US 2021/0291359 A1    Sep. 23, 2021

(30) Foreign Application Priority Data

Aug. 8, 2018 (JP) .................................. 2018-149686

(51) Int. Cl.
*F16H 25/20* (2006.01)
*B25J 9/10* (2006.01)
(Continued)

(52) U.S. Cl.
CPC .............. *B25J 9/106* (2013.01); *B25J 9/102* (2013.01); *B25J 9/104* (2013.01); *F15B 15/20* (2013.01);
(Continued)

(58) Field of Classification Search
CPC ........ B25J 9/102; B25J 9/106; B25J 17/0241; B25J 9/144; B25J 9/0006;
(Continued)

(56) References Cited

U.S. PATENT DOCUMENTS 10,576,624 B2 *  3/2020  Nagatsuka ............... B25J 9/106
11,046,425 B2 *  6/2021  Wagner .................... F16H 25/20
(Continued)

FOREIGN PATENT DOCUMENTS

| CN | 109070355 A | 12/2018 |
| EP | 3437809 A1 | 2/2019 |

(Continued)

OTHER PUBLICATIONS

International Search Report and Written Opinion of PCT Application No. PCT/JP2019/029633, dated Oct. 1, 2019, 09 pages of ISRWO.

*Primary Examiner* — Gregory Robert Weber
(74) *Attorney, Agent, or Firm* — CHIP LAW GROUP

(57) ABSTRACT

A link structure (1) includes: a first link (2); a target member to be moved (housing) (3) that is provided in the interior of the first link (2), and that is movable in the interior of the first link (2); a movement mechanism (4) that is fixed to the first link (2), and that is configured to cause the target member to be moved (3) to move in movement directions (M1, M2) along the first link (2) in response to power of a power part; and an action part (6) that is provided to the target member to be moved (3), and that is configured to act on a movement of a second link (8) mounted onto the first link (2).

8 Claims, 7 Drawing Sheets

(51) Int. Cl.
  *F15B 15/20* (2006.01)
  *F16H 19/04* (2006.01)
  *F16H 19/06* (2006.01)
(52) U.S. Cl.
  CPC ......... *F16H 19/04* (2013.01); *F16H 19/0618* (2013.01); *F16H 25/20* (2013.01); *F16H 2025/204* (2013.01); *F16H 2025/2031* (2013.01); *F16H 2025/2081* (2013.01)
(58) Field of Classification Search
  CPC ....... F16H 2025/204; F16H 2025/2031; F16H 2025/2043; F16H 2025/2037; F16H 2025/2034
  USPC ........................................................ 74/89.33
  See application file for complete search history.

(56) References Cited

U.S. PATENT DOCUMENTS

| | | | |
|---|---|---|---|
| 11,440,637 B2* | 9/2022 | Lorenz | F16H 19/06 |
| 2008/0229860 A1* | 9/2008 | Bonev | B25J 9/106 |
| | | | 74/479.01 |
| 2010/0229669 A1* | 9/2010 | Kim | B25J 18/00 |
| | | | 74/490.01 |
| 2011/0061481 A1* | 3/2011 | Zimmermann | F24S 30/452 |
| | | | 74/89.23 |
| 2012/0048685 A1* | 3/2012 | Chen | B65G 25/02 |
| | | | 198/750.1 |
| 2013/0104686 A1* | 5/2013 | Yamazaki | B25J 17/00 |
| | | | 74/490.05 |
| 2017/0067548 A1* | 3/2017 | Neuhaus | H02P 1/00 |
| 2018/0172121 A1* | 6/2018 | Potter | B25J 17/0241 |
| 2018/0290295 A1* | 10/2018 | Nagatsuka | B25J 17/00 |
| 2019/0118371 A1 | 4/2019 | Sasaki et al. | |
| 2019/0168400 A1* | 6/2019 | Kamon | B25J 9/106 |
| 2019/0240832 A1* | 8/2019 | Kawaguchi | B25J 15/10 |
| 2019/0381677 A1* | 12/2019 | Kamon | B25J 9/106 |

FOREIGN PATENT DOCUMENTS

| | | | | |
|---|---|---|---|---|
| JP | 2007-307686 A | | 11/2007 | |
| JP | 2007307686 A | * | 11/2007 | |
| JP | 6105024 B2 | * | 3/2017 | ............. B25J 17/00 |
| JP | 2018083255 A | | 5/2018 | |
| KR | 10-2019-0002433 A | | 1/2019 | |
| WO | 2008/136402 A1 | | 11/2008 | |
| WO | 2012/070547 A1 | | 5/2012 | |
| WO | 2017/170619 A1 | | 10/2017 | |
| WO | WO-2017170629 A1 | | 10/2017 | |
| WO | 2018-075121 A | | 5/2018 | |

* cited by examiner

LINK STRUCTURE

CROSS REFERENCE TO RELATED APPLICATIONS

This application is a U.S. National Phase of International Patent Application No. PCT/JP2019/029633 filed on Jul. 29, 2019, which claims priority benefit of Japanese Patent Application No. JP 2018-149686 filed in the Japan Patent Office on Aug. 8, 2018. Each of the above-referenced applications is hereby incorporated herein by reference in its entirety.

FIELD

The present disclosure relates to a link structure.

BACKGROUND

Link structures are used for joints, such as knees and elbows, of robots. Patent Literature 1 discloses a medical support arm apparatus including an arm made up of a plurality of links.

CITATION LIST

Patent Literature

Patent Literature 1: JP 2018-75121 A

SUMMARY

Technical Problem

In the conventional technique mentioned above, however, when the links used for rotary joints of knees and elbows of robots are driven by a linear motion mechanism, the links are put under a load. Thus, it is desired to reduce the load caused in response to driving of the links.

Consequently, the present disclosure proposes a link structure capable of reducing the load caused in response to driving of the links.

Solution to Problem

To solve the problem described above, a link structure includes: a first link; a target member to be moved that is provided in an interior of the first link, the target member to be moved being movable in the interior of the first link; a movement mechanism fixed to the first link, the movement mechanism being configured to cause the target member to be moved to move in movement directions along the first link in response to power of a power part; and an action part provided to the target member to be moved, the action part being configured to act on a movement of a second link mounted onto the first link.

Advantageous Effects of Invention

According to the present disclosure, a link structure can be provided that is capable of reducing the load caused in response to driving of the links. The effects described herein are not necessarily limited, and may be any one of the effects described in the present disclosure.

DESCRIPTION OF EMBODIMENTS

Embodiments of the present disclosure will be described below with reference to the drawings. In the following embodiments, the same reference signs are given to the same parts, thereby omitting overlapping descriptions.

First Embodiment

Application Example of Link Structure According to Present Disclosure

Figure 1:
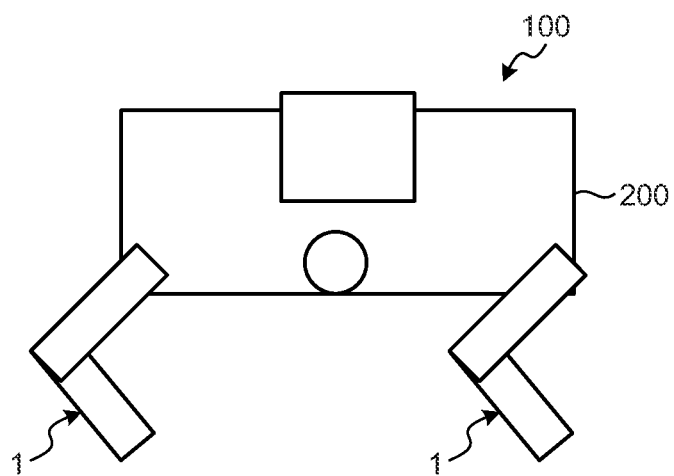
FIG. 1 is a view illustrating an example of a robot to which a technique according to the present disclosure is applied.

FIG. 1 is a view illustrating an example of a robot to which a technique according to the present disclosure is applied. A robot 100 illustrated in FIG. 1 has link structures 1 and a main body 200 to which the link structures 1 are provided. In the example illustrated in FIG. 1, the robot 100 has two link structures 1 provided to the main body 200. The link structures 1 function, for example, as rotary joints of the robot 100. The link structures 1 are an example of a linear motion actuator for driving the rotary joints of the robot 100. The rotary joints include joints, such as knees and elbows, of the robot 100, for example. The main body 200 has a control device that controls driving of the link structures 1.

Constitution Example of Link Structure according to First Embodiment

Figure 2:
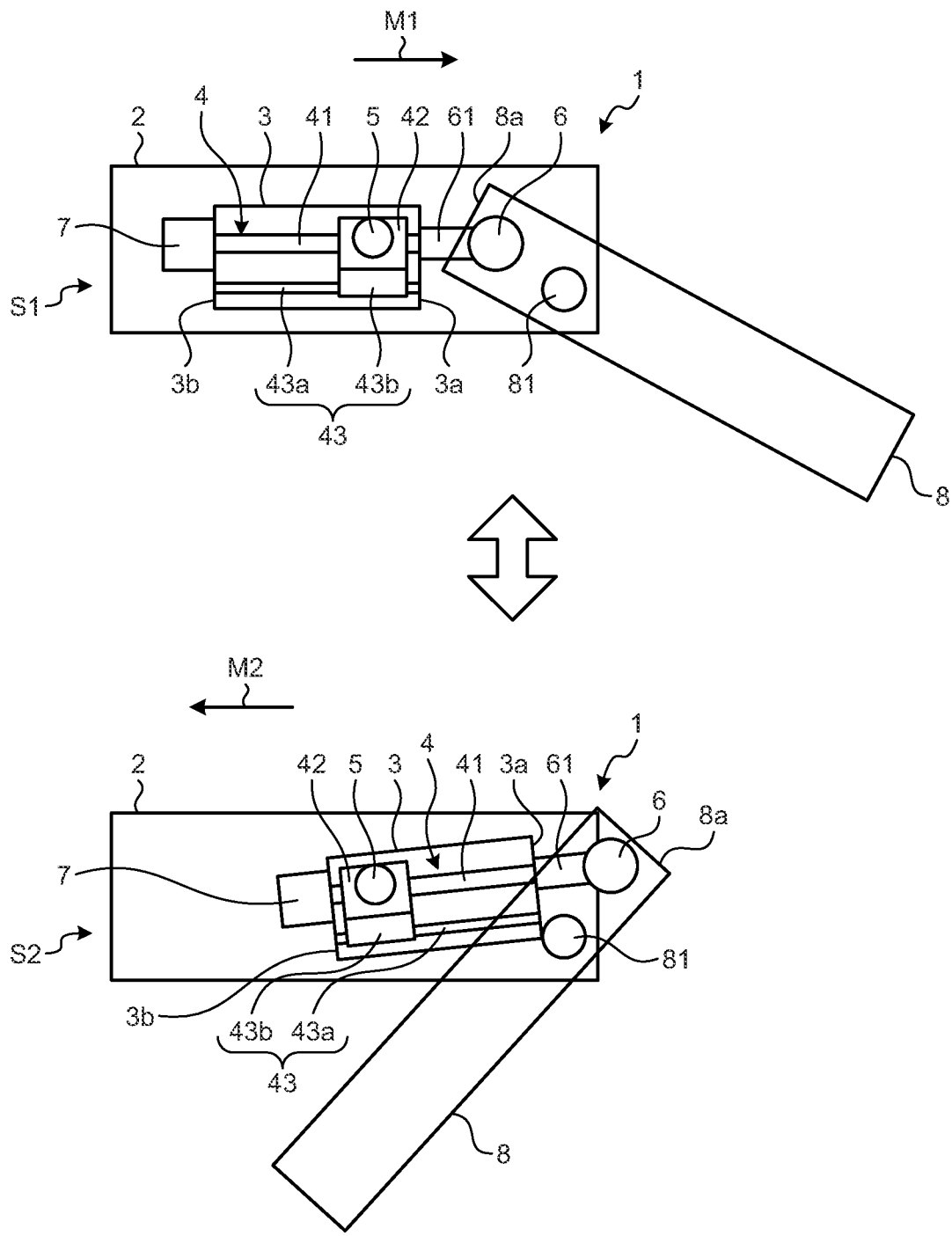
FIG. 2 is a view illustrating an example of a constitution of a link structure according to a first embodiment.
Figure 3:
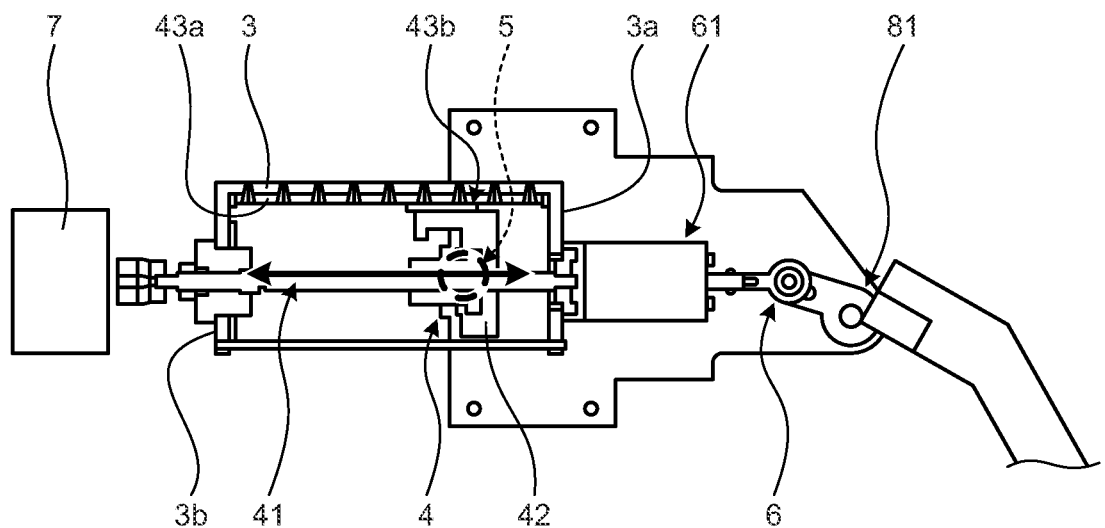
FIG. 3 is a schematic sectional diagram of the link structure according to the first embodiment.
Figure 4:
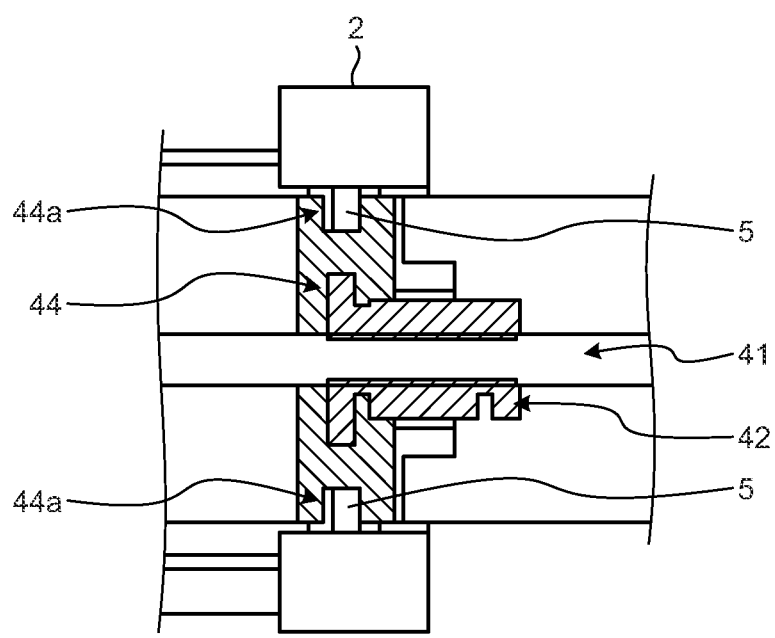
FIG. 4 is a schematic diagram illustrating an example of a fixing structure of the link structure according to the first embodiment.

FIG. 2 is a view illustrating an example of a constitution of the link structure 1 according to a first embodiment. FIG. 3 is a schematic sectional diagram of the link structure 1 according to the first embodiment. FIG. 4 is a schematic diagram illustrating an example of a fixing structure of the link structure 1 according to the first embodiment.

As illustrated in FIG. 2 and FIG. 3, the link structure 1 has a first link 2, a housing 3, a movement mechanism 4, a rotation part 5, an action part 6, a power part 7, and a second link 8. For example, the link structure 1 has a structure in which, by driving the action part 6 to move linearly, the second link 8 coupled to the first link 2 in a rotatable manner is driven to rotate.

The first link 2 is fixed to the main body 200 of the robot 100. The first link 2 is, for example, a rod-shaped hollow frame. The first link 2 can be formed by a member of a synthetic resin or metal, for example. In the present embodiment, the first link 2 is a fixed link that is fixed to the main body 200, but is not limited thereto.

The housing 3 is provided in the interior of the first link 2. The housing 3 can be formed by a member of a synthetic resin or metal, for example. The housing 3 is formed to have such a size and a shape as to be movable in the interior of the first link 2. The housing 3 is an example of a target member to be moved. The housing 3 is caused to move to movement directions M1, M2 along the longitudinal direction of the first link 2. The movement direction M1 is, for example, a direction in which the housing 3 is moved so as to bend the second link 8 with respect to the first link 2. The movement direction M2 is, for example, a direction in which the housing 3 is moved so as to straighten the second link 8 with respect to the first link 2.

The movement mechanism 4 is fixed to the first link 2. The movement mechanism 4 causes, in the interior of the first link 2, the housing 3 to move in response to power of the power part 7 in the movement direction M1 and the movement direction M2 along the first link 2. The movement mechanism 4 causes the housing 3 to move in order to rotate the second link 8 coupled to the first link 2. In the present embodiment, the movement mechanism 4 is described for the case in which the movement mechanism 4 is a mechanism for linear motion driving.

In the example illustrated in FIG. 2 and FIG. 3, the movement mechanism 4 has a screw shaft 41, a nut 42, and a guide part 43. The screw shaft 41 is provided in the interior of the housing 3, and extends along the movement direction M1 and the movement direction M2. As illustrated in FIG. 3, the screw shaft 41 is supported by the housing 3 at both ends thereof in a rotatable manner. The screw shaft 41 is coupled to an output shaft of the power part 7. While being supported by the housing 3, the screw shaft 41 is rotated by the power of the power part 7. The screw shaft 41 has helical screw grooves formed on its surface. In the present embodiment, the movement mechanism 4 is described for the case in which the screw shaft 41 is supported at both ends, but is not limited thereto. For example, the movement mechanism 4 may be a mechanism having a cantilever screw shaft 41.

Into the nut 42, the screw shaft 41 is inserted. The nut 42 has screw grooves formed on its inner periphery and meshing with the screw grooves of the screw shaft 41. The nut 42 is fixed to the first link 2, and is prevented from moving in the movement directions M1, M2 along the longitudinal direction of the first link 2. The nut 42 serves as the starting point of the link structure 1.

The guide part 43 is a guide member provided along the screw shaft 41. The guide part 43 is parallel to the screw shaft 41, and causes the housing 3 to move along the longitudinal direction of the first link 2. For the guide part 43, a linear guide can be used, for example. The guide part 43 has a rail 43a and a block 43b. The rail 43a is, for example, a linear rail. The rail 43a is provided to the housing 3 so as to be parallel to the screw shaft 41. The block 43b is fixed to the nut 42. The block 43b is assembled to the rail 43a, and is configured to be slidable along the rail 43a. In the present embodiment, the link structure 1 has the guide part 43 provided in the movement mechanism 4, which improves the stiffness of the movement mechanism 4 that causes the housing 3 to move. In the present embodiment, the guide part 43 is described for the case in which the guide part 43 has the single rail 43a, but may have a plurality of rails, for example.

The movement mechanism 4 has a coupling plate 44 fixed to the nut 42, as illustrated in FIG. 4. The coupling plate 44 is a coupling member that couples the nut 42 to the first link 2. The coupling plate 44 has a bearing 44a for supporting the rotation part 5 projecting from the first link 2. In the example illustrated in FIG. 4, the bearing 44a is formed at the upper end and the lower end of the coupling plate 44 in the vertical direction. In the movement mechanism 4, the bearing 44a supports the rotation part 5 projecting from the first link 2, thereby preventing the nut 42 from moving in the movement directions M1, M2 along the longitudinal direction of the first link 2.

The rotation part 5 is fixed to the first link 2, and projects toward the movement mechanism 4. The rotation part 5 is, for example, a rotation axis formed into a cylindrical column. The rotation part 5 is supported by the bearing 44a of the coupling plate 44 of the movement mechanism 4, so as to function as the rotation center of the housing 3 and the movement mechanism 4. That is, the housing 3 and the movement mechanism 4 are configured to, when the second link 8 is rotated as illustrated in FIG. 2, be rotatable with the rotation part 5 serving as the rotation center.

As illustrated in FIG. 2 and FIG. 3, the action part 6 is provided to the housing 3, and acts on the movement of the second link 8 mounted onto the first link 2. The action part 6 is a member for supporting the second link 8 in a rotatable manner. The action part 6 includes, for example, a spherical bearing and a spherical sliding bearing. The action part 6 is provided to a first end 3a of the housing 3 in the longitudinal direction of the first link 2, through an attaching part 61. The movement of the housing 3 causes the action part 6 to move together with the housing 3 in the interior of the first link 2. In the present embodiment, the action part 6 is described for the case in which the action part 6 is provided to the housing 3 through the attaching part 61, but is not limited thereto. For example, the action part 6 may be fixed directly to the first end 3a of the housing 3.

The power part 7 outputs power for rotating the screw shaft 41 of the movement mechanism 4. The power part 7 includes, for example, a motor. The power part 7 is provided to a second end 3b of the housing 3 in the longitudinal direction of the first link 2. The output shaft of the power part 7 is coupled to the screw shaft 41. The power part 7 is supplied with electric power from a power supply, which is not illustrated, and is driven under the control of the control device or the like of the main body 200.

The second link 8 is mounted onto the first link 2 in a rotatable (movable) manner. The second link 8 is, for example, a rod-shaped hollow frame. The second link 8 can be formed of a synthetic resin or metal, for example. In the present embodiment, the second link 8 is a movable link that is moved by the first link 2. The second link 8 is coupled in a rotatable manner to the action part 6 provided to the housing 3. That is, the second link 8 is a link moved by the action of the action part 6. The second link 8 is coupled in a rotatable manner to a rotary joint 81 provided to the first link 2. The second link 8 is rotated with the rotary joint 81 serving as the rotation center by the movement of the action part 6 provided to the housing 3 of the first link 2. That is, the rotary joint 81 functions as a point of application to rotate the second link 8.

In the present embodiment, the link structure 1 is described for the case in which the link structure 1 has the second link 8, but is not limited thereto. For example, the second link 8 may be a constituent of the robot 100 instead of being a constituent of the link structure 1.

Operations of Link Structure according to First Embodiment

Exemplary operations of the link structure 1 according to the first embodiment will be described next. In a state S1 illustrated in FIG. 2, in the link structure 1, when the power part 7 generates power for movement in the movement direction M1, the screw shaft 41 of the movement mechanism 4 is rotated in a first direction. In the link structure 1, because the nut 42 of the movement mechanism 4 is fixed to the first link 2, rotation of the screw shaft 41 does not cause the nut 42 to move, but the housing 3 supporting the screw shaft 41 is moved toward the movement direction M1 in response to the rotation of the screw shaft 41. In the link structure 1, the housing 3 moving toward the movement direction M1 also causes the action part 6 to move toward the movement direction M1, thereby causing an end 8a of the second link 8 to move. In the link structure 1, in response to the movement of the action part 6 of the first link 2, the second link 8 is then rotated with the rotary joint 81 serving as the rotation center. In the link structure 1, when the housing 3 is moved in the movement direction M1 by driving the power part 7, the nut 42 is rotated around the rotation part 5 as the nut 42 comes closer to the power part 7, in the interior of the first link 2. As a result, in the link structure 1, the housing 3 is rotated together with the nut 42, so that the first end 3a of the housing 3 comes closer to an inner face of the first link 2. As a result, the link structure 1 enters a state in which the second link 8 is bent with respect to the first link 2, as illustrated in a state S2 of FIG. 2.

In the state S2 illustrated in FIG. 2, in the link structure 1, when the power part 7 generates power for movement in the movement direction M2, the screw shaft 41 of the movement mechanism 4 is rotated in a second direction opposite to the first direction. In the link structure 1, because the nut 42 of the movement mechanism 4 is fixed to the first link 2, rotation of the screw shaft 41 does not cause the nut 42 to move, but the housing 3 supporting the screw shaft 41 is moved toward the movement direction M2 in response to the rotation of the screw shaft 41. In the link structure 1, the housing 3 moving toward the movement direction M2 also causes the action part 6 to move toward the movement direction M2, thereby causing the end 8a of the second link 8 to move. In the link structure 1, in response to the movement of the action part 6 of the first link 2, the second link 8 is then rotated with the rotary joint 81 serving as the rotation center. As a result, the link structure 1 enters a state in which the second link 8 is straightened with respect to the first link 2, as illustrated in the state S1 of FIG. 2.

As described above, in the link structure 1 according to the first embodiment, a ball screw is used as the movement mechanism 4 that transfers linear motion driving force, and the nut 42 is fixed to the first link 2. In the link structure 1, the nut 42 and the rotation part 5 serving as the starting point of the link structure 1 are located close to each other as one. In the link structure 1, the action part 6 is located at the first end 3a of the housing 3, and the power part 7 is located at the second end 3b of the housing 3 on the other side. In the link structure 1, rotation of the screw shaft 41 of the movement mechanism 4 causes the housing 3 to move in the movement directions M1, M2, thereby driving the second link 8 to rotate. That is, in the link structure 1, the movement mechanism 4 is fixed to the first link 2, and the movement mechanism 4 serves as the starting point of the link structure 1, to enable the housing 3 to which the action part 6 is provided to be moved. Thus, stress applied to the action part 6 by the second link 8 is transferred to the housing 3, so that the link structure 1 can reduce the load on the movement mechanism 4 fixed to the first link 2. As a result, because the link structure 1 can reduce the load on the movement mechanism 4 for linear motion driving, the movement mechanism 4 can be downsized and simplified.

In the link structure 1 according to the present embodiment, the rotation part 5 is fixed to the first link 2, and with the rotation part 5 serving as the rotation center, the housing 3 and the movement mechanism 4 can be rotated in the interior of the first link 2. Thus, the rotation part 5 causes the housing 3 and the movement mechanism 4 to rotate in the interior of the first link 2, so that the link structure 1 can extend the range of motion of the action part 6. As a result, the link structure 1 can reduce the load on the movement mechanism 4, and can also extend the range of motion of the second link 8 with respect to the first link 2.

In the link structure 1 according to the present embodiment, the movement mechanism 4 has the screw shaft 41 to be held by the housing 3, and the nut 42 can be fixed to the first link 2. Thus, the link structure 1 can reduce the buckling moment load on the nut 42, enabling the guide part 43 to be made smaller and lighter in order to improve stiffness. As a result, the link structure 1 can be made smaller and lighter. Additionally, the nut 42 of the movement mechanism 4 serving as the starting point and the rotation part 5 are located close to each other as one, which enables the link structure 1 to further reduce the buckling moment load on the nut 42. Furthermore, because the link structure 1 reduces the load on the nut 42, the link structure 1 can reduce backlash between the screw shaft 41 and the nut 42.

In the link structure 1 according to the present embodiment, the movement mechanism 4 can have the screw shaft 41 supported by the housing 3 at both ends. Thus, the link structure 1 enables the housing 3 to be moved together with the screw shaft 41 in the interior of the first link 2. As a result, the link structure 1 can ensure durability of the screw shaft 41 even if the screw shaft 41 supported by the housing 3 is made longer, so that the moving range of the housing 3 can be extended.

In the link structure 1 according to the present embodiment, the movement mechanism 4 can be provided with the guide part 43 parallel to the screw shaft 41. Thus, the link structure 1 enables the screw shaft 41 and the guide part 43 to move the housing 3. As a result, the link structure 1 can improve the stiffness of the movement mechanism that moves the housing 3.

In the link structure 1 according to the present embodiment, the power part 7 can be provided to the housing 3 in the interior of the first link 2. Thus, the link structure 1 does not have to provide the power part 7 to the outside, for example, to the main body 200, by providing the power part 7 to the housing 3 in the interior of the first link 2. As a result, the link structure 1 can be applied to more targets, and convenience can be increased.

The link structure 1 according to the first embodiment has been described for the case in which the link structure 1 has the first link 2, the housing 3, the movement mechanism 4, the rotation part 5, the action part 6, the power part 7, and the second link 8, but is not limited thereto. For example, the link structure 1 may have the first link 2, the housing 3, the movement mechanism 4, the rotation part 5, the action part 6, and the power part 7, and the second link 8 may be deleted from the constituents. For example, the second link 8 may be a constituent of the robot 100. Additionally, when the link structure 1 causes the housing 3 to move linearly in the interior of the first link 2 and does not cause the housing 3 and the movement mechanism 4 to rotate, the rotation part 5 can be deleted from the constituents.

The first embodiment described above has been illustrated by way of example, various changes and applications are possible.

First Modification of First Embodiment

Figure 5:
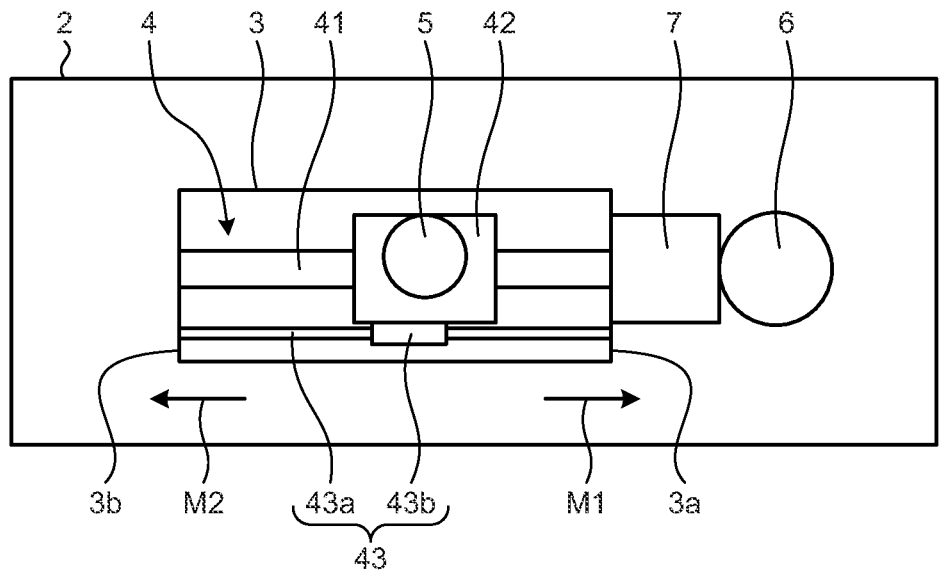
FIG. 5 is a view illustrating an example of a constitution of a link structure according to a first modification of the first embodiment.

For example, in the link structure 1 according to the first embodiment, the location of the power part 7 can be changed. FIG. 5 is a view illustrating an example of a constitution of the link structure 1 according to a first modification of the first embodiment.

As illustrated in FIG. 5, the link structure 1 according to the first modification has the first link 2, the housing 3, the movement mechanism 4, the rotation part 5, the action part 6, and the power part 7. The link structure 1 has the power part 7 positioned between the housing 3 and the action part 6. That is, the power part 7 is provided to the first end 3a of the housing 3 on the movement direction M1 side in the interior of the first link 2. The action part 6 is provided to the power part 7 fixed to the housing 3, so that the action part 6 is provided to the housing 3 through the power part 7. In the first modification, the power part 7 is located between the nut 42 of the movement mechanism 4 and the action part 6.

In the link structure 1 according to the first modification of the first embodiment, when the power part 7 generates power for movement in the movement direction M1, the screw shaft 41 of the movement mechanism 4 is rotated in the first direction. In the link structure 1, because the nut 42 of the movement mechanism 4 is fixed to the first link 2, rotation of the screw shaft 41 does not cause the nut 42 to move, but the housing 3 supporting the screw shaft 41 is moved toward the movement direction M1 in response to the rotation of the screw shaft 41. In the link structure 1, the housing 3 moving toward the movement direction M1 also causes the action part 6 to move toward the movement direction M1, thereby acting on the movement of the second link 8. As with the first embodiment, in the link structure 1, the movement of the housing 3 causes the second link 8 to rotate.

In the link structure 1 according to the first modification, the power part 7 can be located between the nut 42 of the movement mechanism 4 and the action part 6. Thus, by providing the power part 7 to the first end 3a of the housing 3, the link structure 1 can reduce a larger amount of the housing 3 swaying because of the power part 7, for example, than the case in which the power part 7 is provided to the second end 3b of the housing 3. As a result, because the link structure 1 can reduce the load on the movement mechanism 4 for linear motion driving, the movement mechanism 4 can be downsized and simplified. Furthermore, the link structure 1 according to the first modification can reduce the footprint of the housing 3 compared with the case in which the power part 7 is provided to the second end 3b of the housing 3, so that the housing 3 can also be applied to a small-sized first link 2.

Second Modification of First Embodiment

Figure 6:
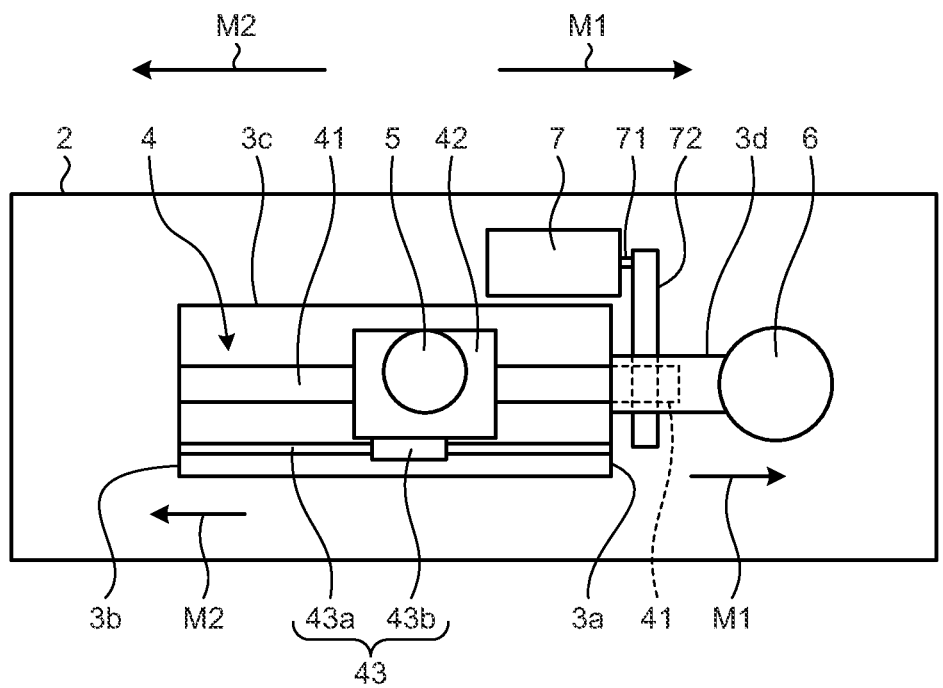
FIG. 6 is a view illustrating an example of a constitution of a link structure according to a second modification of the first embodiment.

For example, in the link structure 1 according to the first embodiment, the location of the power part 7 can be changed further. FIG. 6 is a view illustrating an example of a constitution of the link structure 1 according to a second modification of the first embodiment.

As illustrated in FIG. 6, the link structure 1 according to the second modification has the first link 2, the housing 3, the movement mechanism 4, the rotation part 5, the action part 6, and the power part 7. The link structure 1 has the power part 7 provided to an outer face 3c of the housing 3. The outer face 3c of the housing 3 is a lateral face of the housing 3 coupling the first end 3a to the second end 3b. In the example illustrated in FIG. 6, the power part 7 is located parallel to the screw shaft 41 of the movement mechanism 4 and the inner face of the first link 2 in the longitudinal direction. The power part 7 has an output shaft 71 and a transfer part 72. The output shaft 71 outputs power for rotating the screw shaft 41 of the movement mechanism 4. The transfer part 72 is coupled to the output shaft 71, and transfers power of the output shaft 71 to the screw shaft 41 of the movement mechanism 4.

For the transfer part 72, a belt mechanism can be used. For example, a first gear provided to the output shaft 71 and a second gear provided to the screw shaft 41 are coupled by a belt, and the transfer part 72 causes the screw shaft 41 of the movement mechanism 4 to rotate in response to rotation of the output shaft 71. Additionally, the first end 3a of the housing 3 has a projection 3d supporting the screw shaft 41 in a rotatable manner. The transfer part 72 is inserted into the projection 3d, and is coupled to the screw shaft 41.

In the link structure 1 according to the second modification of the first embodiment, when the power part 7 generates power for movement in the movement direction M1, the screw shaft 41 of the movement mechanism 4 is rotated in the first direction through the transfer part 72. In the link structure 1, because the nut 42 of the movement mechanism 4 is fixed to the first link 2, rotation of the screw shaft 41 does not cause the nut 42 to move, but the housing 3 supporting the screw shaft 41 is moved toward the movement direction M1 in response to the rotation of the screw shaft 41. In the link structure 1, the housing 3 moving toward the movement direction M1 also causes the action part 6 to move toward the movement direction M1, thereby acting on the movement of the second link 8. As with the first embodiment, in the link structure 1, the movement of the housing 3 causes the second link 8 to rotate.

In the link structure 1 according to the second modification, the power part 7 can be provided to the outer face 3c of the housing 3. Thus, by providing the power part 7 to the outer face 3c of the housing 3, the link structure 1 can reduce a larger amount of the housing 3 swaying because of the power part 7, for example, than the case in which the power part 7 is provided to the second end 3b of the housing 3. As a result, because the link structure 1 can reduce the load on the movement mechanism 4 for linear motion driving, the movement mechanism 4 can be downsized and simplified. Furthermore, the link structure 1 can reduce the footprint of the housing 3, so that the housing 3 can also be applied to a small-sized first link 2.

Third Modification of First Embodiment

Figure 7:
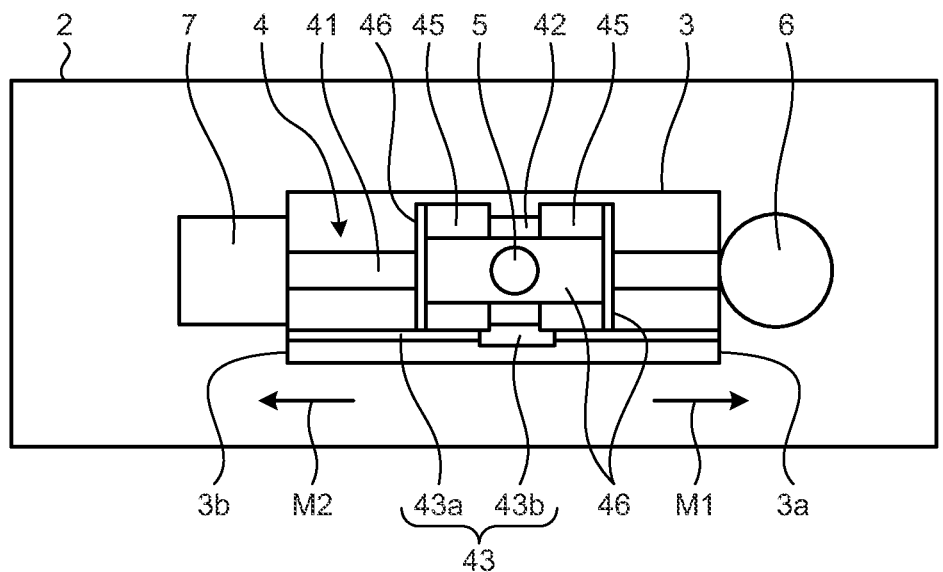
FIG. 7 is a view illustrating an example of a constitution of a link structure according to a third modification of the first embodiment.

For example, in the link structure 1 according to the first embodiment, the constitution of the movement mechanism 4 can be changed further. FIG. 7 is a view illustrating an example of a constitution of the link structure 1 according to a third modification of the first embodiment.

As illustrated in FIG. 7, the link structure 1 according to the third modification has the first link 2, the housing 3, the movement mechanism 4, the rotation part 5, the action part 6, and the power part 7. The movement mechanism 4 has the screw shaft 41, the nut 42, the guide part 43, and detection parts 45. The detection parts 45 are provided to the nut 42, and detects force acting on the nut 42. The detection parts 45 are provided, for example, to both ends of the nut 42 on the movement direction M1 side and the movement direction M2 side. For the detection parts 45, a coil spring for detecting strain or a distance sensor, for example, can be used. The detection parts 45 are mounted onto both sides of the nut 42 in the longitudinal direction of the housing 3 by mounting members 46. The detection parts 45 detect force acting on the nut 42, and outputs the detection result to the control device or the like of the main body 200. In the example illustrated in FIG. 7, the link structure 1 has been described for the case in which the detection parts 45 are used at both sides of the nut 42, but the link structure 1 may have the detection part 45 provided to either of the two sides.

In the link structure 1 according to the third modification of the first embodiment, when the power part 7 generates power for movement in the movement direction M1, the screw shaft 41 of the movement mechanism 4 is rotated in the first direction through the transfer part 72. In the link structure 1, because the nut 42 of the movement mechanism 4 is fixed to the first link 2, rotation of the screw shaft 41 does not cause the nut 42 to move, but the housing 3 supporting the screw shaft 41 is moved toward the movement direction M1 in response to the rotation of the screw shaft 41. In the link structure 1, the housing 3 moving toward the movement direction M1 also causes the action part 6 to move toward the movement direction M1, thereby acting on the movement of the second link 8. As with the first embodiment, in the link structure 1, the movement of the housing 3 causes the second link 8 to rotate. Additionally, once the detection parts 45 have detected force acting on the housing 3, the link structure 1 outputs the detected result to the control device or the like of the main body 200. Thus, the control device or the like of the main body 200 can control the power part 7 on the basis of the result detected by the detection parts 45 of the movement mechanism 4.

In the link structure 1 according to the third modification, the detection parts 45 can detect the force acting on the nut 42 of the movement mechanism 4. Thus, in the link structure 1, the detection parts 45 can detect the nut 42 of the movement mechanism 4 having come into contact with the housing 3. This enables movement control based on positional relation between the housing 3 and the nut 42, and the link structure 1 can avoid an increase in footprint of the housing 3 resulting from the housing 3 and the nut 42 coming into contact with each other.

Second Embodiment

Constitution Example of Link Structure according to Second Embodiment

Figure 8:
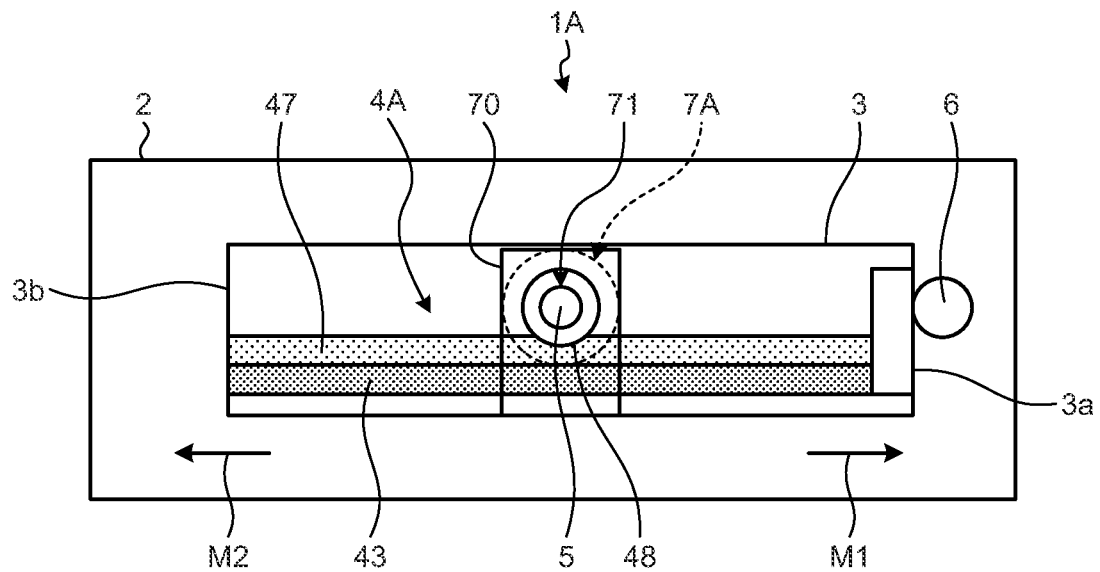
FIG. 8 is a view illustrating an example of a constitution of a link structure according to a second embodiment.

FIG. 8 is a view illustrating an example of a constitution of a link structure 1A according to a second embodiment. As illustrated in FIG. 8, the link structure 1A has the first link 2, the housing 3, a movement mechanism 4A, the rotation part 5, the action part 6, and a power part 7A. For example, by driving the action part 6 to move linearly, the link structure 1A can drive the second link 8 coupled to the first link 2 to rotate.

The movement mechanism 4A is fixed to the first link 2. The movement mechanism 4A causes, in the interior of the first link 2, the housing 3 to move in response to power of the power part 7A in the movement direction M1 and the movement direction M2 along the first link 2. The movement mechanism 4A causes the housing 3 to move in order to rotate the second link 8 coupled to the first link 2. In the present embodiment, the movement mechanism 4 is a mechanism for linear motion driving.

In the example illustrated in FIG. 8, the movement mechanism 4A has a rack 47, a pinion 48, and the guide part 43. The rack 47 is a member made by toothing a flat bar. The rack 47 is provided running from the first end 3a to the second end 3b of the housing 3 in the interior of the housing 3. The rack 47 extends along the movement directions M1, M2. The pinion 48 is a circular gear. The pinion 48 is coupled to the output shaft 71 of the power part 7A. The pinion 48 is in mesh with the rack 47.

The guide part 43 is a guide member provided along the rack 47. The guide part 43 is parallel to the rack 47, and causes the housing 3 to move in the movement direction M1 and the movement direction M2 along the first link 2. For the guide part 43, a linear guide can be used, for example. The guide part 43 causes the rack 47 and the housing 3 to move in the movement directions M1, M2. When the pinion 48 is rotated in response to driving of the power part 7A, the movement mechanism 4A causes the rack 47 and the housing 3 to move in the movement directions M1, M2 in response to the rotation.

The power part 7A outputs power for rotating the pinion 48 of the movement mechanism 4. The power part 7A includes, for example, a motor. The power part 7A is fixed to the first link 2, for example, and is not configured to move in the interior of the first link 2. The output shaft 71 of the power part 7A is coupled to the pinion 48 of the movement mechanism 4. The power part 7A is integral with the rotation part 5 described above and is provided to the first link 2 as a drive unit 70. The power part 7A is supplied with electric power from a power supply, which is not illustrated, and is driven under the control of the control device of the main body 200.

In the link structure 1A, the second link 8 described above is mounted onto the first link 2 in a rotatable manner. The link structure 1A is configured to rotate the second link 8 by movement of the action part 6 provided to the housing 3 of the first link 2.

Operations of Link Structure according to Second Embodiment

Exemplary operations of the link structure 1A according to the second embodiment will be described next. In the link structure 1A, when the power part 7A generates power for movement in the movement direction M1, the rack 47 is moved in the movement direction M1 in response to rotation of the pinion 48 of the movement mechanism 4A. In the link structure 1A, in response to the movement of the rack 47, the housing 3 is also moved in the movement direction M1. In the link structure 1A, the housing 3 moving toward the movement direction M1 also causes the action part 6 to move toward the movement direction M1, thereby causing the second link 8 described above to move.

In the link structure 1A, when the power part 7A generates power for movement in the movement direction M2, the rack 47 is moved in the movement direction M2 in response to rotation of the pinion 48 of the movement mechanism 4. In the link structure 1A, in response to the movement of the rack 47, the housing 3 is also moved in the movement direction M2. In the link structure 1A, the housing 3 moving toward the movement direction M2 also causes the action part 6 to move toward the movement direction M2, thereby causing the second link 8 described above to move.

As described above, in the link structure 1A according to the present embodiment, the movement mechanism 4A and the power part 7A are fixed to the first link 2, and the movement mechanism 4A and the power part 7A serve as the starting point of the link structure 1A, to enable the housing 3 to which the action part 6 is provided to be moved. In other words, in the link structure 1A, the power part 7A and the rotation part 5 is fixed to the first link 2 as the starting point, and the movement mechanism 4A can cause the housing 3 to move. Thus, stress from the action part 6 is transferred to the housing 3, so that the link structure 1A can reduce the load on the movement mechanism 4A fixed to the first link 2. As a result, because the link structure 1A can reduce the load on the movement mechanism 4A for linear motion driving, the movement mechanism 4A can be downsized and simplified.

The link structure 1A according to the second embodiment has been described for the case in which the link structure 1A has the first link 2, the housing 3, the movement mechanism 4A, the rotation part 5, the action part 6, and the power part 7A, but is not limited thereto. For example, the link structure 1A may have the second link 8 described above as a constituent. Additionally, when the link structure 1A causes the housing 3 to move linearly in the interior of the first link 2 and does not cause the housing 3, the movement mechanism 4A, and the power part 7A to rotate, the rotation part 5 can be deleted from the constituents.

Third Embodiment

Constitution Example of Link Structure according to Third Embodiment

Figure 9:
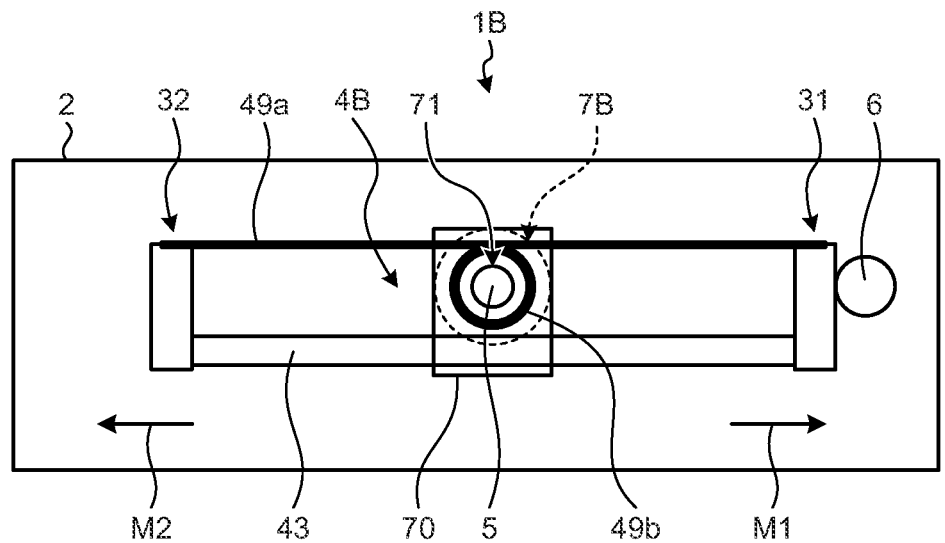
FIG. 9 is a view illustrating an example of a constitution of a link structure according to a third embodiment.
Figure 10:
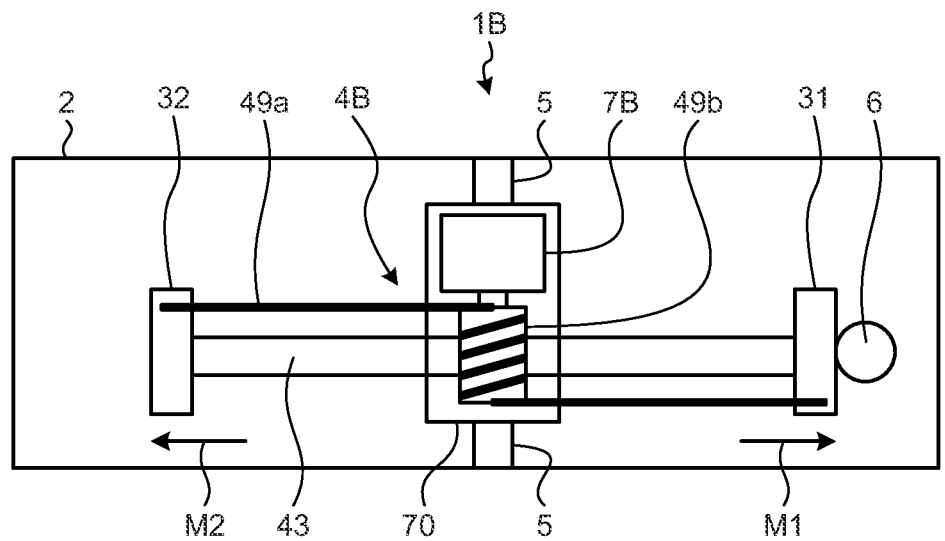
FIG. 10 is a schematic diagram illustrating an example of a fixing structure of the link structure according to the third embodiment.

FIG. 9 is a view illustrating an example of a constitution of a link structure 1B according to a third embodiment. FIG. 10 is a schematic diagram illustrating an example of a fixing structure of the link structure 1B according to the third embodiment.

As illustrated in FIG. 9 and FIG. 10, the link structure 1B has the first link 2, two mobile objects 31, 32, a movement mechanism 4B, the rotation part 5, the action part 6, and a power part 7B. For example, by driving the action part 6 to move linearly, the link structure 1B can drive the second link 8 coupled to the first link 2 to rotate.

The two mobile objects 31, 32 are provided in the interior of the first link 2 so as to sandwich the movement mechanism 4B therebetween. The two mobile objects 31, 32 are caused to move to movement directions M1, M2 along the longitudinal direction of the first link 2. The two mobile objects 31, 32 are an example of a target member to be moved. In the present embodiment, the mobile object 31 is provided on the movement direction M1 side in the longitudinal direction of the first link 2. The mobile object 32 is provided on the movement direction M2 side in the longitudinal direction of the first link 2. The two mobile objects 31, 32 are moved in the movement directions M1, M2 by the movement mechanism 4B.

In the present embodiment, the link structure 1B is described for the case in which the two mobile objects 31, 32 are provided in the interior of the first link 2, but is not limited thereto. For example, in the link structure 1B, only one mobile object of the two mobile objects 31, 32 may be provided, or the mobile objects 31, 32 may be replaced with the rectangular housing 3 described above.

The movement mechanism 4B is fixed to the first link 2. The movement mechanism 4B causes, in the interior of the first link 2, the two mobile objects 31, 32 to move in response to power of the power part 7B in the movement direction M1 and the movement direction M2 along the first link 2. The movement mechanism 4B causes the two mobile objects 31, 32 to move in order to rotate the second link 8 coupled to the first link 2. In the present embodiment, the movement mechanism 4B is a mechanism for linear motion driving.

In the example illustrated in FIG. 9 and FIG. 10, the movement mechanism 4B has a wire 49a, a winding part 49b, and the guide part 43. The wire 49a is provided along the movement directions M1, M2, and one end is fixed the mobile object 31 and the other end is fixed to the mobile object 32. The wire 49a is a member for moving the mobile objects 31, 32 in the movement directions M1, M2 in the interior of the first link 2. The winding part 49b is fixed to the first link 2 between the mobile object 31 and the mobile object 32. The winding part 49b is coupled to the output shaft 71 of the power part 7B. The winding part 49b winds up the wire 49a in a direction according to driving of the power part 7B, and locates the mobile objects 31, 32 closer or at a distance, thereby causing the mobile objects 31, 32 to move in the movement directions M1, M2.

The guide part 43 is a guide member provided along the longitudinal direction of the first link 2. The guide part 43 has the mobile objects 31, 32 fixed to both ends thereof. The guide part 43 is parallel to the first link 2, and causes the mobile objects 31, 32 to move. For the guide part 43, a linear guide can be used, for example. The guide part 43 causes the mobile objects 31, 32 to move in the movement directions M1, M2. When the wire 49a fixed to the mobile object 31 is wound up, the guide part 43 causes the mobile object 32 to move toward the movement direction M2 by feeding the wire 49a fixed to the mobile object 32. When the wire 49a fixed to the mobile object 32 is wound up, the guide part 43 causes the mobile object 31 to move toward the movement direction M1 by feeding the wire 49a fixed to the mobile object 31. That is, when the winding part 49b is rotated in response to driving of the power part 7B, the movement mechanism 4B causes the mobile objects 31, 32 to move in the movement directions M1, M2 in response to the rotation.

The power part 7B outputs power for rotating the winding part 49b of the movement mechanism 4B. The power part 7B includes, for example, a motor. The power part 7B is fixed to the first link 2, for example, and is not configured to move in the interior of the first link 2. The output shaft 71 of the power part 7B is coupled to the winding part 49b of the movement mechanism 4. The power part 7B is integral with the rotation part 5 described above and is provided to the first link 2 as the drive unit 70. The power part 7B is supplied with electric power from a power supply, which is not illustrated, and is driven under the control of the control device of the main body 200.

In the link structure 1B, the second link 8 described above is mounted onto the first link 2 in a rotatable manner. The link structure 1B is configured to rotate the second link 8 by the movement of the action part 6 provided to the housing 3 of the first link 2.

Operations of Link Structure according to Third Embodiment

Exemplary operations of the link structure 1B according to the third embodiment will be described next. In the link structure 1B, when the power part 7B generates power for movement in the movement direction M1, the wire 49a is wound up so as to bring the mobile object 32 closer in response to rotation of the winding part 49b of the movement mechanism 4B. As a result, in the link structure 1B, the mobile object 32 and the guide part 43 are moved in the movement direction M1, causing the mobile object 31 also to move in the movement direction M1. In the link structure 1A, the housing 3 moving toward the movement direction M1 also causes the action part 6 to move toward the movement direction M1, thereby causing the second link 8 described above to move.

In the link structure 1B, when the power part 7 generates power for movement in the movement direction M2, the wire 49a is wound up so as to bring the mobile object 31 closer in response to rotation of the winding part 49b of the movement mechanism 4B. As a result, in the link structure 1B, the mobile object 31 and the guide part 43 are moved in the movement direction M2, causing the mobile object 32 also to move in the movement direction M2. In the link structure 1B, the housing 3 moving toward the movement direction M2 also causes the action part 6 to move toward the movement direction M1, thereby causing the second link 8 described above to move.

As described above, in the link structure 1B according to the present embodiment, the movement mechanism 4B is fixed to the first link 2, and the movement mechanism 4B serves as the starting point of the link structure 1B, to enable the mobile object 31 to which the action part 6 is provided to be moved. In other words, in the link structure 1B, the power part 7B and the rotation part 5 are fixed to the first link 2 as the starting point, and the movement mechanism 4B can cause the mobile objects 31, 32 to move. Thus, stress from the action part 6 is transferred to the mobile objects 31, 32, so that the link structure 1B can reduce the load on the movement mechanism 4B fixed to the first link 2. As a result, because the link structure 1B can reduce the load on the movement mechanism 4B for linear motion driving, the movement mechanism 4B can be downsized and simplified.

Fourth Embodiment

Constitution Example of Link Structure according to Fourth Embodiment

Figure 11:
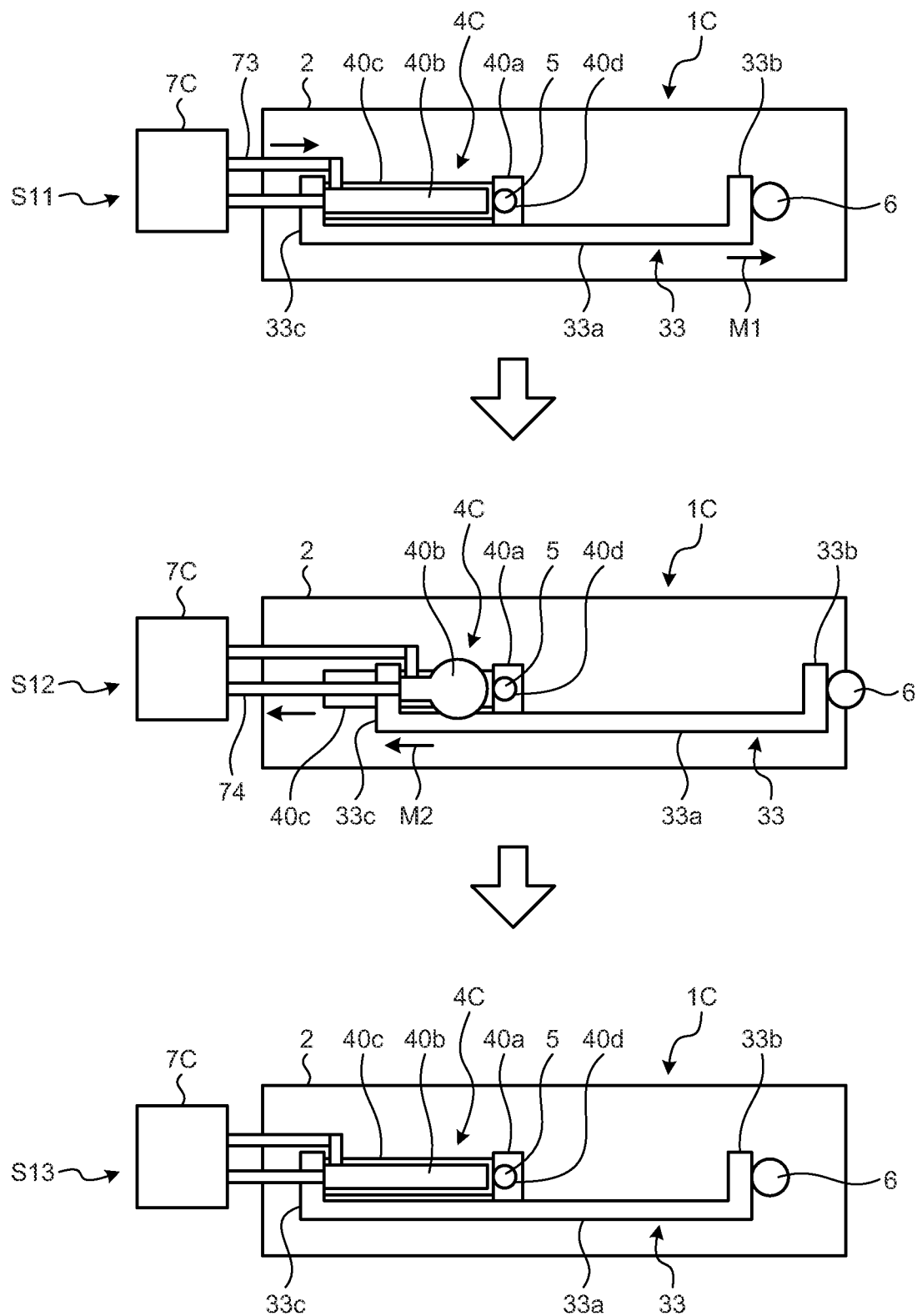
FIG. 11 is a view illustrating an example of a constitution of a link structure according to a fourth embodiment.

FIG. 11 is a view illustrating an example of a constitution of a link structure 1C according to a fourth embodiment.

As illustrated in FIG. 11, the link structure 1C has the first link 2, a mobile object 33, a movement mechanism 4C, the rotation part 5, the action part 6, and a power part 7C. For example, by driving the action part 6 to move linearly, the link structure 1C can drive the second link 8 coupled to the first link 2 to rotate.

The mobile object 33 has a base 33a and ends 33b, 33c, and is formed as one. The mobile object 33 is caused to move in movement directions M1, M2 along the longitudinal direction of the first link 2. The mobile object 33 is an example of a target member to be moved. The base 33a is formed in a rod along the longitudinal direction of the first link 2. The end 33b is provided at the end of the base 33a on the movement direction M1 side, along a direction intersecting the base 33a. The end 33b has the action part 6 provided thereto. The end 33c is provided at the end of the base 33a on the movement direction M2 side, along a direction intersecting the base 33a.

In the present embodiment, the link structure 1C is described for the case in which the two ends 33b, 33c are provided to the base 33a, but is not limited thereto. For example, the link structure 1C may have the end 33b alone to which the action part 6 is provided.

The movement mechanism 4C is provided in the interior of the first link 2. The movement mechanism 4C causes, in the interior of the first link 2, the mobile object 33 to move in response to power of the power part 7C in the movement direction M1 and the movement direction M2. The power part 7C has a constitution to deliver a fluid to the movement part 7C and discharge a fluid from the movement mechanism 4C, for example. The movement mechanism 4C causes the mobile object 33 to move in order to rotate the second link 8 coupled to the first link 2.

The movement mechanism 4C has a fixed part 40a, an elastic part 40b, and a guide part 40c. The fixed part 40a is fixed to the first link 2. The fixed part 40a is fixed to the first link 2, and is prevented from moving in the movement directions M1, M2 along the longitudinal direction of the first link 2. The fixed part 40a serves as the starting point of the link structure 1. The fixed part 40a has a bearing 40d for supporting the rotation part 5 projecting from the first link 2. In the movement mechanism 4C, the bearing 40d supports the rotation part 5 projecting from the first link 2, thereby preventing the fixed part 40a from moving in the movement directions M1, M2 along the longitudinal direction of the first link 2.

The elastic part 40b is provided running from the mobile object 33 to the fixed part 40a. The elastic part 40b functions as, for example, an artificial muscle that expands and contracts by air pressure. The elastic part 40b is formed of rubber or carbon fiber, for example. The elastic part 40b can be achieved as, for example, an antagonistic pneumatic actuator that has an extensile vacuole in an inner layer and a contractile vacuole in the exterior. The elastic part 40b expands in a direction intersecting the longitudinal direction of the first link 2 as a result of injection of a fluid, such as the air, thereby causing the mobile object 33 to move in the movement direction M1. The elastic part 40b contracts as a result of discharge of the fluid in the expanded state, thereby causing the mobile object 33 to move in the movement direction M2.

The guide part 40c is a guide member provided along the longitudinal direction of the first link 2. The guide part 43 is parallel to the first link 2, and causes the mobile object 33 to move. For the guide part 40c, a linear guide can be used, for example. The guide part 40c causes the mobile object 33 to move in the movement directions M1, M2. When the elastic part 40b expands or contracts in response to power from the power part 7C, the movement mechanism 4C causes the mobile object 33 to move in the movement directions M1, M2 in response to the expansion or contraction.

The link structure 1C is operated by output from the power part 7C connected to the movement mechanism 4C. The power part 7C controls the movement mechanism 4C to inject a fluid to the elastic part 40b and discharge the fluid from the elastic part 40b. The power part 7C has pipes 73, 74 connected to the elastic part 40b. The pipe 73 is a flow passage through which a fluid to be injected to the elastic part 40b flows. The pipe 74 is a flow passage through which a fluid to be discharged from the elastic part 40b flows. The power part 7C controls opening and closing of valves and the like provided to the pipes 73, 74, thereby causing the elastic part 40b to expand or contract. In the present embodiment, the link structure 1C is described for the case in which the power part 7C is provided outside of the first link 2, but the power part 7C may be provided in the interior of the first link 2.

In the link structure 1C, the second link 8 described above is mounted onto the first link 2 in a rotatable manner. The link structure 1C is configured to rotate the second link 8 by the movement of the action part 6 provided to the housing 3 of the first link 2.

Operations of Link Structure according to Fourth Embodiment

Exemplary operations of the link structure 1C according to the fourth embodiment will be described next. In a state S11, in the link structure 1C, a fluid is injected to the elastic part 40b of the movement mechanism 4C through the pipe 73 by the power part 7C, which causes the elastic part 40b to expand in the short side direction of the first link 2 in the link structure 1C. As a result, in the link structure 1C, contractile force by which the elastic part 40b contracts in the longitudinal direction of the first link 2 is generated, and this contractile force becomes a driving force for moving the mobile object 33. That is, in the link structure 1C, the contraction of the elastic part 40b causes the mobile object 33 to move toward the movement direction M1.

In a state S12, in the link structure 1C, the fluid is being discharged from the expanded elastic part 40b through the pipe 74 under the control of the power part 7C. As a result, in the link structure 1C, the elastic part 40b contracts in the short side direction of the first link 2, and expansile force is generated in the elastic part 40b in the longitudinal direction of the first link 2. That is, in the link structure 1C, the expansile force causes the elastic part 40b that has contracted to expand in the movement direction M2, thereby causing the mobile object 33 to move toward the movement direction M2. In the link structure 1C, as illustrated by a state S13, once the elastic part 40b returns to the state before the expansion, the mobile object 33 finishes being moved.

As described above, in the link structure 1C according to the present embodiment, the movement mechanism 4C is fixed to the first link 2, and the fixed part 40a of the movement mechanism 4C serves as the starting point of the link structure 1C, to enable the mobile object 33 to which the action part 6 is provided to be moved. In other words, in the link structure 1C, the fixed part 40a and the rotation part 5 are fixed to the first link 2 as the starting point, and the movement mechanism 4C can cause the mobile object 33 to move. Thus, stress from the action part 6 is transferred to the mobile object 33 and the elastic part 40b, so that the link structure 1C can reduce the load on the fixed part 40a of the movement mechanism 4C fixed to the first link 2. As a result, because the link structure 1C can reduce the load on the movement mechanism 4C for linear motion driving, the movement mechanism 4C can be downsized and simplified.

In the present embodiments described above, the link structures 1, 1A, 1B, 1C have been described on the assumption that the first link 2 is fixed, but is not limited thereto. For example, the link structures 1, 1A, 1B, 1C may be provided to the robot 100 in a movable manner.

In the present embodiments described above, the link structures 1, 1A, 1B, 1C have been described for the case in which the second link 8 is rotated with respect to the first link 2, but is not limited thereto. For example, the link structures 1, 1A, 1B, 1C may be configured to cause the second link to expand or contract with respect to the first link 2.

Although the embodiments of the present disclosure have been described above, the embodiments are not intended to limit the technical scope of the present disclosure, and various changes may be made without departing from the spirit of the present disclosure. The components of different embodiments and modifications can also be combined as appropriate.

The effects of the embodiments described herein have been presented by way of example only, and other effects may be possible.

The present technique can also have such constitutions as follows.

(1)

A link structure comprising:

a first link;

a target member to be moved that is provided in an interior of the first link, the target member to be moved being movable in the interior of the first link;

a movement mechanism fixed to the first link, the movement mechanism being configured to cause the target member to be moved to move in movement directions along the first link in response to power of a power part; and an action part provided to the target member to be moved, the action part being configured to act on a movement of a second link mounted onto the first link.

(2)

The link structure according to (1), further comprising a rotation part fixed to the first link, the rotation part serving as a rotation center of the target member to be moved and the movement mechanism.

(3)

The link structure according to (1) or (2), wherein the target member to be moved is a housing, and the movement mechanism comprises:

a screw shaft supported by the housing, the screw shaft extending along the movement directions; and a nut into which the screw shaft is inserted, the nut being fixed to the first link.

(4)

The link structure according to (3), wherein the housing supports both ends of the screw shaft.

(5)

The link structure according to (3) or (4), wherein the movement mechanism further comprises a guide part provided along the screw shaft, and the guide part causing the housing to move.

(6)

The link structure according to any one of (3) to (5), further comprising the power part provided to the housing in the interior of the first link, the power part giving the power to cause the housing to move.

(7)

The link structure according to (6), wherein the power part is positioned between the housing and the action part.

(8)

The link structure according to (6), wherein the power part is provided to an outer face of the housing along the screw shaft, and the movement mechanism has a transfer mechanism configured to transfer the power of the power part to the screw shaft.

(9)

The link structure according to any one of (3) to (8), wherein the movement mechanism further comprises a detection part provided to the nut, the detection part being configured to detect force acting on the nut.

(10)

The link structure according to (1) or (2), wherein the movement mechanism comprises:

a rack provided to the target member to be moved, the rack being movable along the movement directions together with the target member to be moved; and a pinion fixed to the first link, the pinion being configured to transfer the power of the power part to the rack.

(11)

The link structure according to (1) or (2), wherein the movement mechanism comprises:

a wire provided running from one end to another end of the target member to be moved along the movement directions, the wire being configured to cause the target member to be moved to move; and a winding part fixed to the first link between the one end and the other end of the target member to be moved, the winding part being configured to wind up the wire to cause the target member to be moved to move in the movement directions.

(12)

The link structure according to (1) or (2), wherein the movement mechanism comprises:

a fixed part fixed to the first link; and an elastic part provided running from the target member to be moved to the fixed part, the elastic part being configured to expand and contract by air pressure, and the target member to be moved is moved by expansion and contraction of the elastic part in the movement directions.

(13)

The link structure according to any one of (1) to (12), further including the second link mounted onto the first link, the second link being configured to be moved by action of the action part.

(14)

A robot including:

a link structure; and a second link configured to be moved by the link structure, the link structure including:

a first link;

a target member to be moved that is provided in an interior of the first link, the target member to be moved being movable in the interior of the first link;

a movement mechanism fixed to the first link, the movement mechanism being configured to cause the target member to be moved to move in movement directions along the first link in response to power of a power part; and an action part provided to the target member to be moved, the action part being configured to act on a movement of a second link mounted onto the first link.

REFERENCE SIGNS LIST 1, 1A, 1B, 1C link structures
2 first link
3 housing
3a first end
3b second end
3c outer face
4, 4A, 4B, 4C movement mechanisms
5 rotation part
6 action part
7, 7A, 7B, 7C power parts
8 second link
31, 32, 33 mobile bodies
40a fixed part
40b elastic part
40c guide part
41 screw shaft
42 nut
43 guide part
43a rail
43b block
44 coupling plate
45 detection parts
47 rack
48 pinion
49a wire
49b winding part
71 output shaft
72 transfer part
100 robot
200 main body
M1, M2 movement directions

The invention claimed is:

1. A link structure, comprising:
a first link;
a target member, wherein
the target member is in an interior of the first link, and
the target member is movable in the interior of the first link;
a movement mechanism fixed to the first link, wherein
the movement mechanism comprises a nut, a screw shaft, and a guide part,
the movement mechanism is configured to control movement of the target member,
the movement of the target member is controlled to move in at least one specific movement direction along the first link based on power from a power part,
the movement mechanism in entirety is inside the target member,
the screw shaft extends along the at least one specific movement direction inside the target member,
the screw shaft is inserted into the nut, and
the guide part extends along an entire surface of the screw shaft;
a rotation part fixed to the first link, wherein
the nut rotates around the rotation part inside the target member,
the rotation part serves as a rotation center of the target member to be moved and the movement mechanism of the target member, and
the target member rotates with the nut, inside the link structure; and
an action part attached to the target member, wherein the action part is configured to act on a movement of a second link mounted onto the first link.

2. The link structure according to claim 1, wherein the target member to be moved is a housing, and the screw shaft is supported by the housing.

3. The link structure according to claim 2, wherein the housing supports both ends of the screw shaft.

4. The link structure according to claim 2, wherein the guide part is configured to control the movement of the housing.

5. The link structure according to claim 2, wherein the power part is attached to the housing in the interior of the first link, and the power part is configured to provide the power to control the movement of the housing.

6. The link structure according to claim 5, wherein the power part is positioned between the housing and the action part.

7. The link structure according to claim 5, wherein
   the power part is provided to an outer face of the housing along the screw shaft, and
   the movement mechanism has a transfer mechanism configured to transfer the power of the power part to the screw shaft.

8. The link structure according to claim 2, wherein the movement mechanism further comprises a detection part provided to the nut, the detection part being configured to detect force acting on the nut.

\* \* \* \* \*